US008591939B2

(12) United States Patent
Saeki et al.

(10) Patent No.: US 8,591,939 B2
(45) Date of Patent: *Nov. 26, 2013

(54) ADHESIVE PREPARATION CONTAINING FENTANYL

(75) Inventors: Yuji Saeki, Ibaraki (JP); Masato Nishimura, Ibaraki (JP); Kensuke Matsuoka, Ibaraki (JP); Takateru Muraoka, Ibaraki (JP); Yoshifumi Hosaka, Ibaraki (JP); Mitsuhiko Hori, Ibaraki (JP); Kazuhisa Ninomiya, Ibaraki (JP); Hitoshi Akemi, Ibaraki (JP); Hidetoshi Kuroda, Ibaraki (JP)

(73) Assignee: Nitto Denko Corporation, Osaka (JP)

( * ) Notice: Subject to any disclaimer, the term of this patent is extended or adjusted under 35 U.S.C. 154(b) by 1117 days.

This patent is subject to a terminal disclaimer.

(21) Appl. No.: 11/196,935

(22) Filed: Aug. 4, 2005

(65) Prior Publication Data

US 2006/0034900 A1     Feb. 16, 2006

(30) Foreign Application Priority Data

Aug. 12, 2004    (JP) ................................. 2004-235649
Jul. 26, 2005    (JP) ................................. 2005-215405

(51) Int. Cl.
*A61K 31/445*      (2006.01)
*A61F 13/02*       (2006.01)

(52) U.S. Cl.
USPC .......................................... 424/448; 514/317

(58) Field of Classification Search
None
See application file for complete search history.

(56) References Cited

U.S. PATENT DOCUMENTS

| | | | |
|---|---|---|---|
| 4,031,894 A | 6/1977 | Urquhart et al. | |
| 4,588,580 A | 5/1986 | Gale et al. | |
| 4,657,982 A * | 4/1987 | Breck et al. .................... | 525/240 |
| 4,806,341 A | 2/1989 | Chien et al. | |
| 4,822,802 A | 4/1989 | Levy et al. | |
| 4,880,416 A | 11/1989 | Horiuchi et al. | |
| 5,175,052 A | 12/1992 | Tokuda et al. | |
| 5,204,109 A | 4/1993 | Akemi et al. | |
| 5,242,951 A | 9/1993 | Akemi et al. | |
| 5,298,258 A | 3/1994 | Akemi et al. | |
| 5,508,038 A * | 4/1996 | Wang et al. .................... | 424/448 |
| 5,656,285 A | 8/1997 | Sablotsky et al. | |
| 5,820,878 A * | 10/1998 | Hirano et al. ................. | 424/449 |
| 5,866,157 A | 2/1999 | Higo et al. | |
| 5,876,746 A * | 3/1999 | Jona et al. ..................... | 424/449 |
| 5,948,433 A | 9/1999 | Burton et al. | |
| 5,985,317 A | 11/1999 | Venkateshwaran et al. | |
| 6,074,665 A | 6/2000 | Horstmann et al. | |
| 6,139,866 A | 10/2000 | Chono et al. | |
| 6,200,596 B1 * | 3/2001 | Schwartzmiller et al. .... | 424/448 |
| 6,348,210 B1 | 2/2002 | Gale | |
| 6,437,038 B1 | 8/2002 | Chen | |
| 6,638,528 B1 | 10/2003 | Kanios | |
| 7,718,188 B2 * | 5/2010 | Ito et al. ........................ | 424/449 |
| 2003/0109819 A1 | 6/2003 | Tsuruda et al. | |
| 2005/0042269 A1 * | 2/2005 | Tateishi et al. ................ | 424/449 |
| 2006/0013865 A1 | 1/2006 | Ito et al. | |
| 2006/0034901 A1 | 2/2006 | Akemi et al. | |
| 2009/0068486 A1 * | 3/2009 | Blackwell et al. ............ | 428/516 |

FOREIGN PATENT DOCUMENTS

| | | |
|---|---|---|
| CA | 2172738 A1 | 4/1995 |
| CN | 1171736 A | 1/1998 |
| EP | 0 337 358 A2 | 10/1989 |
| EP | 0 430 608 B1 | 2/1995 |
| EP | 0788792 A1 | 8/1997 |
| EP | 1 002 838 A1 | 5/2000 |
| EP | 1 159 972 A2 | 12/2001 |
| EP | 1238664 A1 | 9/2002 |
| JP | 01-261328 A | 10/1989 |
| JP | 01-287024 A | 11/1989 |
| JP | 03-220120 A | 9/1991 |
| JP | 03-223212 A | 10/1991 |
| JP | 05-177920 A | 7/1993 |
| JP | 08-502727 A | 3/1996 |
| JP | 09-099050 A | 4/1997 |
| JP | 10-151185 A | 6/1998 |
| JP | 10-152434 A | 6/1998 |
| JP | 2000-344697 A | 12/2000 |
| JP | 2001-029383 A | 2/2001 |
| JP | 2001-199937 A | 7/2001 |
| JP | 2003-226609 A | 8/2003 |
| RU | 2194496 C2 | 12/2002 |
| TW | 200413034 A | 8/2004 |
| WO | WO 94/04109 A1 | 3/1994 |

(Continued)

OTHER PUBLICATIONS

Roy et al. (Journal of Pharmaceutical Sciences vol. 85, No. 5, May 1996).*
"Deterioration of Cross-Linked Polyethylene Due to Water Treeing" (Chapter in National Academy of Sciences' 1972 Annual Report Conference on Electrical Insulation and Dielectric Phenomena.*
Arkon P-100 Product Data Sheet.*
Venkatraman et al., "Skin adhesives and skin adhesion. 1. Transdermal drug delivery systems," *Biomaterials*, 19, 1119-1136 (1998).
Captured from http://www.arakawaeurope.com/pdfs/SIS052002-1. pdf with a date of May 2000 at bottom of capture (U.S. Appl. No. 11/196,936).

(Continued)

*Primary Examiner* — David J Blanchard
*Assistant Examiner* — Garen Gotfredson
(74) *Attorney, Agent, or Firm* — Leydig, Voit & Mayer, Ltd.

(57) ABSTRACT

The present invention provides a Fentanyl-containing percutaneously absorbable adhesive preparation, which is obtained from economic starting materials, has a constitution simpler than that of conventional ones, has sufficient skin permeability, and which permits control of skin permeability by changing the mixing ratio of two kinds of polyisobutylene having different molecular weights, a tackifier and an organic liquid. Specifically, the present invention provides a percutaneously absorbable adhesive preparation comprising a support and an adhesive layer laminated on one surface thereof, wherein the adhesive layer comprises Fentanyl, two kinds of polyisobutylene having different molecular weights, a tackifier and an organic liquid compatible with the aforementioned two kinds of polyisobutylene and the aforementioned tackifier.

8 Claims, 1 Drawing Sheet

(56) References Cited

FOREIGN PATENT DOCUMENTS

| WO | WO 96/16642 A1 | 6/1996 |
| --- | --- | --- |
| WO | WO 00/42958 A1 | 7/2000 |
| WO | WO 01/43729 A1 | 6/2001 |
| WO | WO 03/037393 A1 | 5/2003 |
| WO | WO 2004/035054 A1 | 4/2004 |

OTHER PUBLICATIONS

Bhowmick and Stephens, eds. Handbook of Elastomers, p. 882 (2000).

Chinese Patent Office, Office Action in CN 2005-10089398.1 (Jun. 20, 2008).

Chinese Patent Office, Office Action in CN 2005-10089399.6 (Jul. 18, 2008).

European Patent Office, Office Action setting forth Third Party Observations in EP 05107128.0 (Feb. 12, 2009).

Japanese Patent Office, Office Action in JP 2005-215433 (Jan. 5, 2011).

Japanese Patent Office, Office Action in JP 2005-215433 (Sep. 30, 2010).

Russian Patent Office, Official Action in RU 2005-124859/15 (Jan. 23, 2009).

Russian Patent Office, Official Action in RU 2005-124860/15 (Jan. 23, 2009).

Taiwan Patent Office, Examination Report in Taiwan Patent Application 094126151 (Feb. 8, 2011).

Japanese Patent Office, Notice of Reasons for Refusal in Japanese Patent Application No. 215405/2005 (Feb. 15, 2011).

Canadian Patent Office, Office Action in Canadian Patent Application No. 2,514,636 (Oct. 12, 2011).

Arakawa Kagaku Co. Ltd., *Technical Information of Arkon Series*, (May 2000).

BASF, "Technical Information—Oppanol® B 100, Oppanol® B 150, Oppanol® B 200," *TI/ES 1417 us*: 1-10 (Apr. 2003).

BASF, "Technical Information—Oppanol® B Types," *TI/ES 1482 us*: 1-8 (Sep. 2003).

\* cited by examiner

ADHESIVE PREPARATION CONTAINING FENTANYL

FIELD OF THE INVENTION

The present invention relates to a Fentanyl-containing adhesive preparation for continuous administration of Fentanyl into the body through the skin.

BACKGROUND OF THE INVENTION

Percutaneously absorbable adhesive preparations containing Fentanyl have been already placed in the domestic market in Japan, provided widely for clinical treatments, and making great contribution to the society as a new treatment method for removing pain. The preparation placed in the market is what is called a reservoir type preparation having a complicated structure comprising a drug solution filled between a support and a release controlling membrane, and further, an adhesive layer laminated thereon, so as to control skin permeability of Fentanyl. In foreign countries, too, preparations having various constitutions and the like have been considered and disclosed (U.S. Pat. Nos. 4,588,580, 4,806,341, 4,822,802, 5,656,285, 5,948,433, 5,985,317, 6,074,665).

While the Fentanyl preparations placed in the market show excellent clinical effects and absorption stability during administration, they have complicated constitutions, are very expensive, and economically disadvantageous. To lower the cost even if only slightly, it is necessary to simplify the constitution to lower the step cost and use economical materials.

SUMMARY OF THE INVENTION

It is an object of the present invention to provide a Fentanyl-containing percutaneously absorbable adhesive preparation prepared from economical materials, which has a simpler constitution as compared to conventional preparations and has sufficient function of skin permeability and the like.

The present inventors have conducted intensive studies in an attempt to solve the above-mentioned problems and employed the following constitutions.

That is, the present invention provides the following.
(1) A percutaneously absorbable adhesive preparation comprising a support and an adhesive layer laminated on one surface of the support, wherein the adhesive layer comprises Fentanyl, two kinds of polyisobutylene having different molecular weights, a tackifier and an organic liquid compatible with the aforementioned two kinds of polyisobutylene and the aforementioned tackifier.
(2) The preparation of the above-mentioned (1), wherein Fentanyl is contained in a proportion of 1.5-2.5% of the total weight of the above-mentioned adhesive layer.
(3) The preparation of the above-mentioned (1), wherein the two kinds of polyisobutylene comprises a first polyisobutylene having a viscosity average molecular weight of 600000-1500000 and a second polyisobutylene having a viscosity average molecular weight of 40000-85000.
(4) The preparation of the above-mentioned (1), wherein the tackifier is a polybutene having a number average molecular weight of 900-2900.
(5) The preparation of the above-mentioned (1), wherein the tackifier is an alicyclic saturated hydrocarbon resin having a number average molecular weight of 500-860.
(6) The preparation of the above-mentioned (1) or (3), wherein the two kinds of polyisobutylene comprise a first polyisobutylene and a second polyisobutylene having a smaller molecular weight than that of the first polyisobutylene, at a mixing ratio of the first polyisobutylene:second polyisobutylene of 1:1.2-1:2 by weight.
(7) The preparation of the above-mentioned (1), wherein the tackifier is contained in a proportion of 15-30% of the total weight of the above-mentioned adhesive layer.
(8) The preparation of the above-mentioned (1), wherein the organic liquid is contained in a proportion of not more than 20% of the total weight of the above-mentioned adhesive layer.
(9) The preparation of the above-mentioned (1), wherein the organic liquid is at least one selected from a fatty acid alkyl ester and a branched long-chain alcohol.
(10) The preparation of the above-mentioned (9), wherein the fatty acid alkyl ester is isopropyl myristate and the branched long-chain alcohol is at least one selected from isostearyl alcohol and octyldodecanol.
(11) The preparation of the above-mentioned (9) or (10), wherein the organic liquid comprises a combination of an fatty acid alkyl ester and a branched long-chain alcohol, and a mixing ratio of the fatty acid alkyl ester:branched long-chain alcohol is 1:0.2-1:5 by weight.

EFFECT OF THE INVENTION

Figure 1:
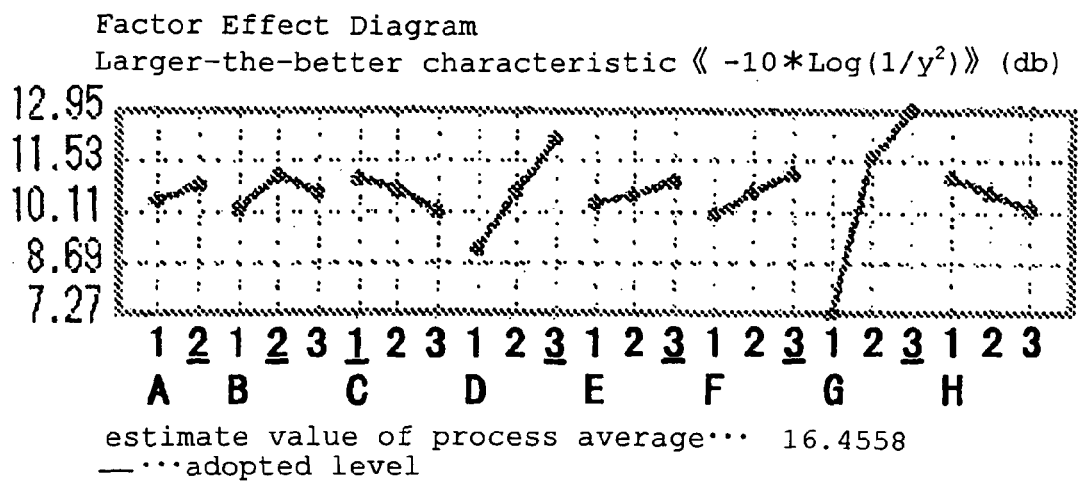
FIG. 1 is a factor effect figure reflecting the analysis results of Experimental Example 2, which shows the SN ratio fluctuation (Table 7) at levels 1 to 2, or 1 to 3 of factors A-G.

The Fentanyl-containing adhesive preparation of the present invention is obtained from economic materials, has a constitution simpler than conventional ones, has sufficient skin permeability, and is capable of controlling skin permeability by changing the mixing ratio of two kinds of polyisobutylene having different molecular weights, a tackifier and an organic liquid. According to the present invention, therefore, a preparation having sufficient function as compared to conventional products can be produced economically, whereby a fine Fentanyl preparation can be provided at a low cost. In addition, a transdermally absorptive preparation having fine appearance, which is free of precipitation of Fentanyl crystals, can be provided, since the solubility of Fentanyl can be increased because an adhesive layer contains an organic liquid.

BEST MODE FOR CARRYING OUT THE INVENTION

The percutaneously absorbable adhesive preparation of the present invention comprises a support and an adhesive layer comprising Fentanyl, two kinds of polyisobutylene having different molecular weights, a tackifier, and an organic liquid compatible with the aforementioned two kinds of polyisobutylene having different molecular weights and the aforementioned tackifier, laminated on one surface of the support. While the preparation can be produced conveniently from common and economical materials, it shows superior properties (e.g., sufficient skin permeability, ability to control skin permeability and the like) comparable to those of the conventional products.

The proportion of Fentanyl relative to the total weight of the adhesive layer is preferably 1.5 to 2.5%, more preferably 1.6 to 2.3%, in view of the relationship between the effect and cost. When the proportion of Fentanyl is less than 1.5%, a sufficient clinical effect cannot be afforded, and when it exceeds 2.5%, crystal precipitation may occur even if the effect is high, which is economically disadvantageous.

The adhesive layer of the present invention contains two kinds of polyisobutylene having different molecular weights. By the "two kinds of polyisobutylene having different molecular weights" is meant a polyisobutylene generally having one peak of molecular weight and a polyisobutylene generally having one peak of molecular weight and a different average molecular weight than the aforementioned polyisobutylene. In the present specification, one of the two kinds of polyisobutylene having different molecular weights is also referred to as a first polyisobutylene and the other polyisobutylene having a smaller molecular weight than that of the first polyisobutylene is also referred to as a second polyisobutylene. As the "two kinds of polyisobutylene having different molecular weights", two kinds of polyisobutylene having different viscosity average molecular weights can be mentioned.

The viscosity average molecular weight in the present invention is determined by calculating a Staudinger-Index ($J_0$) by the Schulz-Blaschke equation from the flow time of capillary 1 of a Ubellohde's viscometer at 20° C. and from the following formula using the $J_0$ value:

$$J_0 = \eta_{sp}/c(1+0.31\eta_{sp}) \text{cm}^3/\text{g(Schulz-Blaschke equation)}$$

$$\eta_{sp} = t/t_0 - 1$$

t: flow time of solution (Hagenbach-couette correction)
$t_0$: flow time of solution (Hagenbach-couette correction)
c: concentration of solution (g/cm$^3$)

$$J_0 = 3.06 \times 10^{-2} \overline{Mv}^{0.65}$$

$\overline{Mv}$: viscosity average molecular weight

In the present invention, two kinds of polyisobutylene having different molecular weights are not particularly limited, but to achieve fine adhesiveness and releaseability of Fentanyl, it is preferable that a first polyisobutylene have a viscosity average molecular weight of 600000-1500000, preferably 700000-1350000, and a second polyisobutylene having a smaller molecular weight than that of the first polyisobutylene have a viscosity average molecular weight of 40000-85000, preferably 45000-65000. Here, when the first polyisobutylene has a viscosity average molecular weight of less than 600000, the inner cohesion necessary for an adhesive layer tends to be unattainable and when it exceeds 1500000, the skin adhesion and tack of the adhesive layer tend to be degraded. Furthermore, when the second polyisobutylene has a viscosity average molecular weight of less than 40000, the adhesive layer becomes sticky to possibly contaminate the skin surface, and when it exceeds 85000, the skin adhesion and tack of the adhesive layer tend to be degraded.

With regard to the two kinds of polyisobutylene having different molecular weights, a mixing ratio of first polyisobutylene:second polyisobutylene having a smaller molecular weight than that of the first polyisobutylene is preferably 1:1.2-1:2, more preferably 1:1.3-1:1.8, by weight. When the mixing ratio of the second polyisobutylene relative to first polyisobutylene is less than 1.2 by weight, the adhesive layer shows markedly decreased skin adhesion, and when the ratio exceeds 2, the adhesive layer shows markedly decreased inner cohesion.

The polyisobutylene exemplified above to be used in the present invention is supplied stably at sufficient economical costs.

The proportion of the two kinds of polyisobutylene having different molecular weights relative to the total weight of the adhesive layer is preferably 50-83%, more preferably 55-78%, in the total weight. The proportion of the first polyisobutylene of the two kinds of polyisobutylene having different molecular weights relative to the whole weight of the adhesive layer is preferably 18-36%, more preferably 22-32%. The proportion of the second polyisobutylene having a smaller molecular weight than that of the first polyisobutylene, relative to the total weight of the adhesive layer is preferably 33-48%, more preferably 35-44%.

The tackifier to be used for the present invention may be appropriately selected from those known in the field of adhesive preparations. As the tackifier, for example, polybutenes, rosin resin, terpene resin, petroleum resin, chroman resin and the like can be mentioned. From the aspects of cost and fine tack, (i) polybutene having a number average molecular weight of 900-2900, preferably 980-2000 (1-butene polymer, 2-butene polymer, copolymer of 1-butene and 2-butene); and (ii) alicyclic saturated hydrocarbon resin having a number average molecular weight of 500-860, preferably 570-710, are preferable. When the number average molecular weight of polybutene of the above-mentioned (i) is less than 900, the adhesive layer becomes sticky, thus possibly posing problems in terms of handling property, and when it exceeds 2900, the effect of the tackifier is difficult to show, and the tack of the adhesive layer tends to decrease. When the number average molecular weight of the alicyclic saturated hydrocarbon resin of the above-mentioned (ii) is less than 500, the adhesive layer tends to be sticky and when it exceeds 860, compatibility becomes inferior.

The number average molecular weight in the present invention is measured by the GPC method and V.P.O method.

As the alicyclic saturated hydrocarbon resin of the above-mentioned (ii), for example, commercially available hydrogenation petroleum resins manufactured by Arakawa Chemical Industries, Ltd., such as ARCON P-70, ARCON P-900, ARCON P-100 etc., and the like can be mentioned.

The tackifier may be used in a combination of one or more kinds thereof.

The proportion of the tackifier relative to the total weight of the adhesive layer is preferably 15-30%, more preferably 16-28%. When the proportion of the tackifier is less than 15%, the tack may be poor, and when it exceeds 30%, the adhesive layer may unpreferably show a propensity toward destruction.

The organic liquid to be used in the present invention is not particularly limited as long as it is compatible with the above-mentioned two kinds of polyisobutylene having different molecular weights and the above-mentioned tackifier. For example, a fatty acid alkyl ester, a branched long-chain alcohol and the like can be mentioned.

As the fatty acid alkyl ester, for example, a fatty acid alkyl ester comprising a higher fatty acid preferably having 12 to 16, more preferably 12 to 14, carbon atoms and a lower monovalent alcohol having 1 to 4 carbon atoms can be mentioned. As the above-mentioned higher fatty acid, preferred are lauric acid (C12), myristic acid (C14) and palmitic acid (C16), and myristic acid is more preferable.

As the above-mentioned lower monovalent alcohol, for example, straight chain and branched chain alcohols having 1 to 4 carbon atoms can be mentioned. Specific examples include methyl alcohol, ethyl alcohol, propyl alcohol, isopropyl alcohol, butyl alcohol and the like, with preference given to isopropyl alcohol. Therefore, the most preferable fatty acid alkyl ester is isopropyl myristate.

As the branched long-chain alcohol, for example, saturated or unsaturated branched long-chain alcohol having 16 to 22, preferably 18 to 20, carbon atoms can be mentioned. Specific examples include isostearyl alcohol, octyldodecanol and the like can be mentioned, with preference given to isostearyl alcohol and octyldodecanol.

When a long-chain alcohol is used as the organic liquid of the present invention, it is preferable to use branched long-chain alcohol. The use of non-branched long-chain alcohol is not preferable because compatibility with polyisobutylene may be sometimes poor.

The organic liquid may be used in a combination of one or more kinds thereof.

As the organic liquid to be used in the present invention, a fatty acid alkyl ester and a branched long-chain alcohol are preferable, and isopropyl myristate, isostearyl alcohol and octyldodecanol are particularly preferable, in view of the Fentanyl absorption enhancing effect and the great contribution to the increased solubility of Fentanyl.

The proportion of the organic liquid relative to the total weight of the adhesive layer is preferably not more than 20%. When the proportion of the organic liquid exceeds 20%, the cohesion of the adhesive layer drastically decreases and cohesive failure tends to occur easily.

In the present invention, the use of a fatty acid alkyl ester and a branched long-chain alcohol in combination as the organic liquid is preferable in view of the solubility of Fentanyl and maintenance of the skin adhesiveness of the adhesive layer. In this case, the mixing ratio of fatty acid alkyl ester and a branched long-chain alcohol is preferably 1:0.2-1:5, more preferably 1:0.4-1:3, by weight.

When the mixing ratio thereof (branched long-chain alcohol:fatty acid alkyl ester) by weight is less than 0.2, the solubility of Fentanyl may become poor, and when it exceeds 5, the skin adhesion during application may be drastically degraded due to the perspiration.

An adhesive constituting the adhesive layer may contain, as optional components, other additives (e.g., esters such as glycerine fatty acid ester, sorbitan fatty acid ester etc., organic solvents having a high boiling point such as dimethyl sulfoxide, N-methylpyrrolidone etc., absorption promoters such as pyrrolidonecarboxylate etc., and the like), as long as the effect of the present invention is not inhibited. The proportion of additives as optional components is preferably not more than 15% of the total weight of the adhesive layer.

The thickness of the adhesive layer is generally 30 μm-300 μm, preferably 60 μm-180 μm.

While the support to be used in the present invention is not particularly limited, those substantially impermeable to drug and the like, namely, those free of a decrease in the content due to the loss of Fentanyl, which is an active ingredient, additives and the like from the adhesive layer through a support are preferable. As the support, for example, single films of polyester, nylon, saran (registered trademark), polyethylene, polypropylene, polyvinyl chloride, ethylene-ethyl acrylate copolymer, polytetrafluoroethylene, Surlyn (registered trademark), metal foil and the like, lamination films of these and the like can be used. Of these, the support is preferably a lamination film of a non-porous plastic film made from the above-mentioned material and a porous film, so as to improve the adhesive force (anchor property) between the support and an adhesive layer. In this case, the adhesive layer is preferably formed on the porous film side.

As such porous film, one capable of improving the anchor property with the adhesive layer can be employed. Specifically, paper, woven fabric, non-woven fabric, knitted fabric, mechanically perforated sheet and the like can be mentioned. Of these, from the aspects of handling property and the like, paper, woven fabric and non-woven fabric are particularly preferable. A porous film having a thickness of 10-200 μm is employed from the aspects of improved anchor property, flexibility of adhesive preparation as a whole, and adhesion operability and the like. In the case of a thin preparation such as a plaster type preparation and a pressure-sensitive adhesive tape type preparation, one having a thickness of 10-100 μm is employed.

When a woven fabric or a non-woven fabric is used as the porous film, the fabric weight is preferably set to 5-30 $g/m^2$, more preferably 6-15 $g/m^2$. In the present invention, the most preferable support is a lamination film of a polyester film (preferably polyethylene terephthalate film) having a thickness of 1.5-6 μm and a non-woven polyester (preferably polyethylene terephthalate) fabric having a fabric weight of 6-12 $g/m^2$.

The percutaneously absorbable adhesive preparation of the present invention preferably have a release liner laminated thereon to protect the adhesive surface of an adhesive layer until use. The release liner is not particularly limited as long as it can be subjected to a peel treatment and certainly has a sufficient peelability. Examples thereof include films of polyester, polyvinyl chloride, polyvinylidene chloride, polyethylene terephthalate and the like, paper such as quality paper, glassine and the like, a laminate film of quality paper, glassine etc. with polyolefin, and the like, which have been subjected to a peel treatment comprising applying silicone resin, fluororesin and the like to the surface to be in contact with the adhesive layer. The thickness of the release liner is generally 10-200 μm, preferably 25-100 μm.

The release liner to be used in the present invention is preferably made from a polyester (particularly, polyethylene terephthalate) resin, from the aspects of barrier property and cost. Moreover, the thickness is more preferably about 25-100 μm.

The form of the percutaneously absorbable adhesive preparation of the present invention is not particularly limited and, for example, a tape, a sheet and the like are mentioned.

The percutaneously absorbable adhesive preparation of the present invention can be produced by, for example, dissolving two kinds of polyisoburylene having different molecular weights, a tackifier, an organic liquid, other additive as an optional component and Phentanyl in a suitable solvent such as toluene etc., applying the obtained adhesive solution to a release liner, drying the liner to form an adhesive layer, and laminating a support on the adhesive layer. Alternatively, they can be produced by, for example, directly applying the above-mentioned adhesive solution to a support and drying the support to form an adhesive layer. When an adhesive solution is applied thick for forming an adhesive layer, the solution may not be dried uniformly. To ensure a certain thickness of the adhesive layer, the adhesive solution may be applied twice or more.

It is preferable to seal the percutaneously absorbable adhesive preparation of the present invention until before use for preservation, transportation and the like. The packaging method includes, for example, superimposing one sheet or several sheets of the percutaneously absorbable adhesive preparation, packing them with a packaging material, and heat-sealing the part surrounding them. The packaging material is not particularly limited and may be, for example, a sheet or a film. From the aspects of easy packaging and air tightness, heat-sealable ones are preferable. Specific examples of suitable packaging materials include those using a plastic sheet having heat sealability, such as polyethylene, Surlyn (registered trademark), ethylene-vinyl acetate copolymer, ethylene-vinyl alcohol copolymer, polyacrylonitrile copolymer, polyvinyl alcohol copolymer and the like. Particularly, a laminate of a gas impermeable film such as polyester film, metal foil and the like is preferably used to prevent volatilization, scattering and the like of Fentanyl, which is an active ingredient, contained in the adhesive preparation. As the packaging material, one having a thickness of generally 10 μm-200 μm is used. Particularly, the above-mentioned packaging material comprising a polyacrylonitrile copolymer having high barrier property in the innermost layer is more preferable. Moreover, out of the fear of degradation of handling property (e.g., easy taking out from a package) caused by the bleeding of the adhesive component and the like, some design may be preferably employed, which is exemplified by an emboss processing of the packaging material, a dry etching processing to somewhat enlarge the aforementioned liner part than the preparation, a package formed by blister molding to reduce the contact area and the like.

The percutaneously absorbable adhesive preparation of the present invention can be used by taking out by tearing the above-mentioned package immediately before use, removing the release liner, and adhering the exposed adhesive surface to the skin surface.

While the dose of the percutaneously absorbable adhesive preparation of the present invention varies depending on the age, body weight, symptom etc. of patients, a preparation containing 2-15 mg of Fentanyl is generally applied to 10-60 $cm^2$ of the skin of an adult about 1 to 3 times per 7 days.

EXAMPLES

The present invention is explained in detail in the following by referring to Examples, which are not to be construed as limitative. In the following, "part" and "%" mean "parts by weight" and "wt %", respectively.

Example and Comparative Example

Manufacture of Samples

The compositions having mixing ratios of Experimental Examples 1-21 shown in the following Table 4 and Table 8 were dissolved in toluene to give a coating solution having a solute concentration of 35%. This solution was applied to a polyethylene terephthalate (PET) liner after a silicone peel treatment such that a Fentanyl content after drying became 2.5 mg/20 $cm^2$. This was dried in a hot-air circulation oven at 100° C. for 3 min to give an adhesive layer.

A non-woven fabric surface of a support made of a 2 μm thick PET film and a PET non-woven fabric (12 g/$m^2$) adhered to each other with a polyester adhesive was laminated on the adhesive layer. The PET liner of this laminate was peeled off and another adhesive layer having the same composition and thickness as above was laminated on the exposed surface, and aged at room temperature for 2 days to give a sheet-like percutaneously absorbable adhesive preparation. In Experimental Examples, Experimental Examples 1 and 17 are Comparative Examples.

Experimental Example 1

Solubility of Fentanyl in Additive

Fentanyl (0.1 g) was measured, each of the additives (1 g) shown in Table 1 was added and the mixture was stirred at room temperature (around 25° C.) for 30 min. (when the drug was completely dissolved, for a short time, the drug was gradually added, and the mixture was stirred further for 30 min after the final addition, wherein the upper limit of the total amount of the drug was 0.3 g). This solution was filtered, the filtrate (0.1 g) was precisely measured, dissolved in methanol, and the amount of Fentanyl dissolved therein was measured by HPLC.

Table 1 shows solubility of Fentanyl in each additive. Therefrom were used isopropyl myristate (IPM:NIKKO CHEMICALS IPM-100) and octyldodecanol (ODO:COGNISco.EUTANOL(R)G) considered to be more preferable for the present invention to perform the following tests. Table 2 shows predicted mixing ratios of these two additives (single use or simultaneous use), which can dissolve Fentanyl. In Table 2, when the additive is IPM alone, the mixing ratio becomes high, causing fear of cohesive failure, and the preparation cannot be produced easily. When ODO is co-used, the ratio becomes small, a cohesive failure does not occur easily, and preparations can be produced by variously changing the mixing ratio of IPM and ODO.

TABLE 1

Solubility of Fentanyl in additive

| No. | additive | Solubility (mg/g)* |
|---|---|---|
| 1 | diisopropyl adipate | 190 |
| 2 | dioctyl adipate | 106 |
| 3 | isostearyl alcohol | 209 |
| 4 | 2-ethyl-1,3-hexanediol | ≧304 |
| 5 | octyldodecanol | 195 |
| 6 | ethyl oleate | 86 |
| 7 | oleyl oleate | 37 |
| 8 | triethyl citrate | 180 |
| 9 | isopropyl palmitate | 63 |
| 10 | sorbitan trioleate | 165 |
| 11 | Polysorbate 80 | 87 |
| 12 | diethyl sebacate | 216 |
| 13 | dibutyl sebacate | 162 |
| 14 | diethyl phthalate | 281 |
| 15 | squalene | 9 |
| 16 | isopropyl myristate | 77 |

*Solubility is the amount of Fentanyl that is dissolved in 1 g of additive (mg)

TABLE 2

| Fentanyl preparation mixing ratio | Matrix weight (mg/10 $cm^2$) | additive | |
|---|---|---|---|
| | | IPM | ODO |
| 1.5% | 167 | 19% | — |
| 1.6% | 156 | 21% | — |
| 1.7% | 147 | 22% | — |
| 1.8% | 139 | 23% | — |
| 1.9% | 132 | 25% | — |
| 2.0% | 125 | 26% | — |
| 2.5% | 100 | 32% | — |
| 1.5% | 167 | — | 8% |
| 1.6% | 156 | — | 8% |
| 1.7% | 147 | — | 9% |
| 1.8% | 139 | — | 9% |
| 1.9% | 132 | — | 10% |
| 2.0% | 125 | — | 10% |
| 2.5% | 100 | — | 13% |
| 1.5% | 167 | 3% | 6% |
| 1.6% | 156 | 3% | 7% |
| 1.7% | 147 | 3% | 8% |
| 1.8% | 139 | 3% | 8% |
| 1.9% | 132 | 3% | 9% |
| 2.0% | 125 | 3% | 9% |
| 2.5% | 100 | 3% | 12% |
| 1.5% | 167 | 5% | 6% |
| 1.6% | 156 | 5% | 6% |
| 1.7% | 147 | 5% | 7% |
| 1.8% | 139 | 5% | 7% |

TABLE 2-continued

| Fentanyl preparation mixing ratio | Matrix weight (mg/10 cm$^2$) | additive IPM | additive ODO |
|---|---|---|---|
| 1.9% | 132 | 5% | 8% |
| 2.0% | 125 | 5% | 8% |
| 2.5% | 100 | 5% | 11% |
| 1.5% | 167 | 7% | 5% |
| 1.6% | 156 | 7% | 5% |
| 1.7% | 147 | 7% | 6% |
| 1.8% | 139 | 7% | 6% |
| 1.9% | 132 | 7% | 7% |
| 2.0% | 125 | 7% | 7% |
| 2.5% | 100 | 7% | 10% |
| 1.5% | 167 | 10% | 4% |
| 1.6% | 156 | 10% | 4% |
| 1.7% | 147 | 10% | 5% |
| 1.8% | 139 | 10% | 5% |
| 1.9% | 132 | 10% | 6% |
| 2.0% | 125 | 10% | 6% |
| 2.5% | 100 | 10% | 9% |

Mixing ratio of additive necessary for dissolving Fentanyl at 2.5 mg/10 cm$^2$
(mixing ratio (%) of additive relative to total Matrix weight necessary for dissolution, calculated from solubility of Fentanyl in IPM: 77 mg/g, solubility of Fentanyl in ODO: 195 mg/g)

Experimental Example 2

Permeation Test of the Skin Removed from Mouse, Analysis of Maximum Permeation Rate and Evaluation of Appearance after Lapse of 3 Months 1. Permeation Test of the Skin Removed from Mouse Percutaneously absorbable adhesive preparations having the composition shown in Experimental Examples 1-18 of Table 4 (various combinations of factor and level shown in Table 3), which were produced by the above-mentioned method, were subjected to a permeation test according to the following method using the skin removed from mouse. For the test, a cell permeation test apparatus was used.

Each preparation was punched out two at a time in φ6 mm to give samples. The skin was removed from 8-week-old (male) mouse. As the receptor solution, 0.15 mol/L citric acid-phosphate buffer was used.
(Permeation Test Method)

One sheet of preparation punched out in φ6 mm (0.2826 cm$^2$) was adhered to the removed skin. The removed skin was set in a diffusion cell by being placed therein with the surface having the adhered preparation facing upward. A receptor solution was fed at about 2.5 ml/hr, and the receptor solution discharged from the diffusion cell was recovered in vial containers as fractions at 4, 5, 6, 7, 8, 9, 12, 15, 18, 21 and 24 hr. After recovery, the weight was accurately measured. The Fentanyl concentration of the recovered solution was measured by HPLC, and the amount of permeation and permeation rate were calculated.

2. Analysis by L18 Experimental Design

The maximum permeation rate of Fentanyl was applied to a factor effect analysis based on the larger-the-better characteristic according to L18 experimental design. Table 3 shows factors and levels, Table 4 shows 18 Experimental Examples based on combination according to the L18 orthogonal table, Table 5 shows the maximum permeation speed in each Experimental Example, Table 6 shows variance analysis results (demonstrating that clearly significant factors are D and G), Table 7 shows the step average, and FIG. 1 shows schematic factor effect of Table 7 in the form of a diagram. In Table 6, factors A-G are controlling factors A-G in Table 3, H and e are errors irrelevant to each factor, T is diffusion of the whole, f is degree of freedom, S is sum of squares, and V is diffusion. In Table 7, factors A-G are controlling factors A-G in Table 3, H is an error irrelevant to the factor, levels 1-3 are levels 1-3 of Table 3, and the numerical values in the Table show SN ratio based on larger-the-better characteristic at each level. The SN ratio based on larger-the-better characteristic was determined by the formula:

$$SN\ \text{ratio}=-10\times\text{Log}(1/y^2)(\text{db}) \text{ wherein } y \text{ is a characteristic value.}$$

The estimated process average in FIG. 1 is an estimate value of the effect expected to be achieved by the combination of most effective levels. In FIG. 1, the underlined levels were employed to obtain the estimated value of process average.

From the results, the skin permeability of the percutaneously absorbable adhesive preparation of the present invention is considered to be controllable by changing the ratio of two kinds of polyisobutylene having different molecular weights, a tackifier, and an additive (organic liquid), which achieves various levels of skin permeability. When compared to the error (row H), FEN concentration and IPM concentration were found have made great contribution to the skin permeability.

The detail of the analysis method according to the L18 experimental design followed "Quality Engineering Course 4 Experiments for Quality Design, Genichi Taguchi, Japanese Standards Association". For the analysis, an analysis software, "RIPSES for windows" RICOH RIPSES DEVELOPMENT G CO., Ltd., was used.

3. Evaluation of Appearance after Lapse of 3 Months

Percutaneously absorbable adhesive preparations having the compositions of Experimental Examples 1-18 were produced by the above-mentioned method and preserved at 25° C., 60% RH for 3 months. The appearance of each preparation after the lapse of 3 months was visually observed and evaluated based on the following criteria.

◎: Fine without precipitation of Fentanyl crystal on the surface of adhesive layer ○: Slight and acceptable level of Fentanyl crystal precipitation is found on the edge of adhesive layer, and generally fine.

x: Fentanyl crystal precipitation is found on the surface of adhesive layer, and defective.

The evaluation results are shown in Table 5. From the result, it is assumed that a preparation produced using a composition containing an organic liquid showed high solubility of Fentanyl due to the presence of the organic liquid, which in turn affords uniform dispersion of Fentanyl in the adhesive layer, and fine appearance. In contrast, a preparation produced using a composition without an organic liquid showed poor solubility of Fentanyl, which allowed precipitation of Fentanyl crystal on the surface of the adhesive layer to degrade the appearance. Due to the precipitation of Fentanyl crystal, moreover, partial degradation of skin adhesion of the preparation was also confirmed. From the foregoing, it was found that the absence of an organic liquid in the adhesive layer results in a preparation having low product value.

Each symbol in Table 3 and Table 4 means the following.

B80: Oppanol(R)B80(BASF) polyisobutylene viscosity average molecular weight 820000

B100: Oppanol(R)B100(BASF) polyisobutylene viscosity average molecular weight 1110000

P100: ARKON(R)P100(Arakawa Chemical Industries, Ltd.) tackifier alicyclic saturated hydrocarbon resin average molecular weight 610

B12: Oppanol(R)B12(BASF) polyisobutylene viscosity average molecular weight 55000

IPM: IPM-100(NIKKO Chemicals) isopropyl myristate

ISO: (Wako Pure Chemical Industries, Ltd.) reagent isostearyl alcohol

FEN: Fentanyl

TABLE 3

Factors and levels

| Control factor | A<br>High molecular weight rubber | B<br>High molecular weight rubber Mixing ratio | C<br>P100 mixing ratio | D<br>IPM Concentration (%)/whole adhesive layer | E<br>Low molecular weight rubber B12 Mixing ratio | F<br>ISO Concentration (%)/whole adhesive layer | G<br>FEN Concentration (%)/whole adhesive layer |
|---|---|---|---|---|---|---|---|
| Level 1 | B80 | 25 | 17 | 0 | 42 | 0 | 1.5 |
| Level 2 | B100 | 30 | 25 | 3 | 50 | 3 | 2 |
| Level 3 | — | 35 | 33 | 5 | 58 | 5 | 2.5 |

In Table 3, B, C and E show mixing ratios D, E and F show (%) relative to the total weight of the adhesive layer.

TABLE 4

| Exp. Ex. No. | FEN | B100 | B80 | B12 | P100 | IPM | ISO | weight of adhesive layer |
|---|---|---|---|---|---|---|---|---|
| 1 | 1.5 | | 29.5 | 49.3 | 19.9 | 0.0 | 0.0 | 0.167 g/10 cm² |
| 2 | 2.0 | | 23.0 | 46.0 | 23.0 | 3.0 | 3.0 | 0.125 g/10 cm² |
| 3 | 2.5 | | 18.9 | 43.8 | 24.9 | 5.0 | 5.0 | 0.100 g/10 cm² |
| 4 | 2.5 | | 29.2 | 48.7 | 16.6 | 0.0 | 3.0 | 0.100 g/10 cm² |
| 5 | 1.5 | | 24.0 | 46.5 | 20.0 | 3.0 | 5.0 | 0.167 g/10 cm² |
| 6 | 2.0 | | 26.6 | 37.2 | 29.2 | 5.0 | 0.0 | 0.125 g/10 cm² |
| 7 | 2.0 | | 33.5 | 40.2 | 16.3 | 3.0 | 5.0 | 0.125 g/10 cm² |
| 8 | 2.5 | | 29.4 | 42.0 | 21.0 | 5.0 | 0.0 | 0.100 g/10 cm² |
| 9 | 1.5 | | 26.5 | 44.0 | 25.0 | 0.0 | 3.0 | 0.167 g/10 cm² |
| 10 | 2.0 | 22.5 | | 52.2 | 15.3 | 5.0 | 3.0 | 0.125 g/10 cm² |
| 11 | 2.5 | 25.1 | | 42.2 | 25.1 | 0.0 | 5.0 | 0.100 g/10 cm² |
| 12 | 1.5 | 22.1 | | 44.2 | 29.2 | 3.0 | 0.0 | 0.167 g/10 cm² |
| 13 | 2.5 | 27.0 | | 52.2 | 15.3 | 3.0 | 0.0 | 0.100 g/10 cm² |
| 14 | 1.5 | 28.0 | | 39.2 | 23.3 | 5.0 | 3.0 | 0.167 g/10 cm² |
| 15 | 2.0 | 24.7 | | 41.2 | 27.2 | 0.0 | 5.0 | 0.125 g/10 cm² |
| 16 | 1.5 | 30.4 | | 43.4 | 14.8 | 5.0 | 5.0 | 0.167 g/10 cm² |
| 17 | 2.0 | 29.1 | | 48.2 | 20.8 | 0.0 | 0.0 | 0.125 g/10 cm² |
| 18 | 2.5 | 29.1 | | 34.9 | 27.5 | 3.0 | 3.0 | 0.100 g/10 cm² |

In Table 4, each numerical value shows mixing wt %.

TABLE 5

Maximum permeation rate (n = 2 average) and evaluation of appearance after lapse of 3 months

| Exp. Ex. No. | Maximum permeation rate (μg/cm²/h) | evaluation of appearance |
|---|---|---|
| 1 | 1.87 | x |
| 2 | 3.70 | ⊙ |
| 3 | 5.09 | ⊙ |
| 4 | 3.87 | ○ |
| 5 | 2.87 | ⊙ |
| 6 | 4.08 | ⊙ |
| 7 | 3.67 | ⊙ |
| 8 | 4.85 | ○ |
| 9 | 1.74 | ⊙ |
| 10 | 4.83 | ⊙ |
| 11 | 3.71 | ⊙ |
| 12 | 1.86 | ⊙ |
| 13 | 4.81 | ○ |
| 14 | 2.89 | ⊙ |
| 15 | 3.59 | ○ |
| 16 | 3.38 | ⊙ |
| 17 | 3.24 | x |
| 18 | 4.70 | ○ |

TABLE 6

| Factor | f | S | V |
|---|---|---|---|
| A | 1 | 1.0968 | 1.0968 |
| B | 2 | 2.6189 | 1.3095 |
| C | 2 | 2.5106 | 1.2553 |
| D | 2 | 28.5568 | 14.2784 |
| E | 2 | 0.9002 | 0.4501 |
| F | 2 | 3.9567 | 1.9784 |
| G | 2 | 105.6941 | 52.8471 |
| H | 2 | 2.4493 | 1.2247 |
| e | 2 | 2.7652 | 1.3826 |
| T | 17 | 150.5486 | |

TABLE 7

| Factor | Level 1 | Level 2 | Level 3 | Total average |
|---|---|---|---|---|
| A | 10.3534 | 10.8471 | | 10.6002 |
| B | 10.1391 | 11.0732 | 10.5883 | |
| C | 10.9893 | 10.715 | 10.0964 | |
| D | 9.058 | 10.5993 | 12.1433 | |
| E | 10.3423 | 10.5707 | 10.8877 | |
| F | 10.0177 | 10.6172 | 11.1658 | |
| G | 7.2653 | 11.5845 | 12.9508 | |
| H | 11.0518 | 10.6006 | 10.1483 | |

Experimental Example 3

Permeation Test of Skin Removed from Mouse and Simulation Analysis of Predicted Human Blood Concentration 1. Permeation Test of Skin Removed from Mouse Percutaneously absorbable adhesive preparations having the compositions of Experimental Examples 19-21 were produced by the above-mentioned method and subjected to a permeation test of the skin removed from mouse. For the test, a cell permeation test apparatus was used.

The preparations were punched out (three at a time) in φ20 mm (preparation application area: 3.14 cm²) to give samples. The skin was removed from 8-week-old (male) mouse. As the receptor solution, 0.15 mol/L citric acid-phosphate buffer was used.

(Permeation Test Method)

As the skin removed from the mouse, normal skin and keratin-removed skin after 20 times of stripping with a cellophane tape were used.

One sheet of preparation punched out in φ20 mm (3.14 cm²) was adhered to the skin removed from mouse. The removed skin was set in a diffusion cell by being placed therein with the surface having the adhered preparation facing upward. A certain amount of the receptor solution was sampled with the lapse of time, the concentration of Fentanyl in the receptor solution was measured by HPLC and the amount of permeation was calculated.

2. Simulation Analysis of Predicted Human Blood Concentration

From the above-mentioned permeation test results of the skin removed from mouse, various parameters (permeation rate and lag time in the fixed-interval state) of normal skin and keratin-removed skin were calculated.

Using the obtained various parameters and the in vivo kinetics parameters in human as determined from the clinical literature data of Fentanyl, Fentanyl blood concentration of human was predicted by an analysis using an analysis software (SKIN-CAD™, Biocom Systems, Inc.)

In Table 8, each symbol shows the following.

H300: INDOPOL(R)H300 (BP Amoco Chemical co.) polybutene umber average molecular weight (GPC)1300

ODO: EUTANOL G NF (Cognis co.) octyldodecanol

FEN, B80, B12 and IPM are similar to those shown in Table 3 and Table 4.

TABLE 8

| Exp. Ex. No. | FEN | B80 | B12 | H300 | IPM | ODO | weight of adhesive layer |
|---|---|---|---|---|---|---|---|
| 19 | 1.7 | 25.2 | 37.9 | 25.2 | 3.0 | 7.0 | 294 mg/20 cm² |
| 20 | 1.7 | 24.7 | 37.0 | 24.6 | 5.0 | 7.0 | 294 mg/20 cm² |
| 21 | 1.7 | 23.8 | 35.7 | 23.8 | 10.0 | 5.0 | 294 mg/20 cm² |

In Table 8, each numerical value shows mixing wt %.

Figure 2:
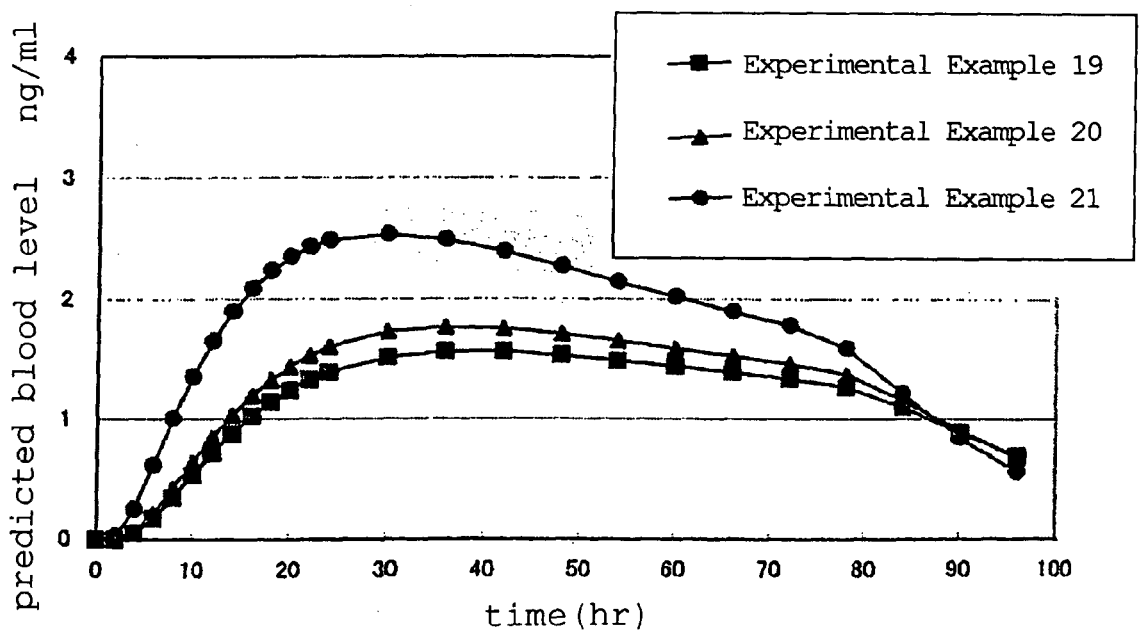
FIG. 2 is a graph reflecting the analysis results of Experimental Example 3, which shows predicted Fentanyl blood concentrations when applied to human. The predicted blood concentration is obtained by correcting the diffusion coefficient and after application of 40 $cm^2 \times 72$ hr.

The results are shown in FIG. 2. The predicted blood concentration was obtained by amending the diffusion coefficient, and relates to the application at 40 cm²×72 hr. From these results, the percutaneously absorbable adhesive preparation of the present invention was confirmed to exhibit sufficient transdermal absorbability even when applied to humans.

This application is based on patent application Nos. 2004-235649 and 2005-215405 filed in Japan, the contents of which are hereby incorporated by reference.

The invention claimed is:

1. A percutaneously absorbable adhesive preparation comprising a support and an adhesive layer laminated on one surface of the support,
wherein the adhesive layer comprises (a) Fentanyl, (b) two kinds of polyisobutylene having different molecular weights, (c) a tackifier, and (d) an organic liquid compatible with the two kinds of polyisobutylene and the tackifier,
wherein the organic liquid comprises a combination of (i) a fatty acid alkyl ester comprising a higher fatty acid having 12 to 16 carbon atoms and a lower monovalent alcohol having 1 to 4 carbon atoms and (ii) a branched long-chain alcohol having 16 to 22 carbon atoms in a ratio of 1:0.2-1:5 by weight,
wherein the fatty acid alkyl ester is isopropyl myristate, and the branched long-chain alcohol is at least one selected from isostearyl alcohol and octyldodecanol,
wherein the organic liquid is present in an amount of not more than 20% of the total weight of the adhesive layer, and
wherein Fentanyl is present in an amount of 1.5-2.5% of the total weight of the adhesive layer.

2. The preparation of claim 1, wherein the two kinds of polyisobutylene comprises a first polyisobutylene having a viscosity average molecular weight of 600000-1500000 and a second polyisobutylene having a viscosity average molecular weight of 40000-85000.

3. The preparation of claim 1, wherein the tackifier is a polybutene having a number average molecular weight of 900-2900.

4. The preparation of claim 1, wherein the tackifier is an alicyclic saturated hydrocarbon resin having a number average molecular weight of 500-860.

5. The preparation of claim 1, wherein the two kinds of polyisobutylene comprise a first polyisobutylene and a second polyisobutylene having a smaller molecular weight than that of the first polyisobutylene, at a mixing ratio of the first polyisobutylene:second polyisobutylene of 1:1.2-1:2 by weight.

6. The preparation of claim 2, wherein the two kinds of polyisobutylene comprise a first polyisobutylene and a second polyisobutylene having a smaller molecular weight than that of the first polyisobutylene, at a mixing ratio of the first polyisobutylene:second polyisobutylene of 1:1.2-1:2 by weight.

7. The preparation of claim 1, wherein the tackifier is present in an amount of 15-30% of the total weight of the adhesive layer.

8. The preparation of claim 1, wherein the branched long-chain alcohol is octyldodecanol.

* * * * *